United States Patent
Feichtner et al.

(10) Patent No.: US 8,535,537 B2
(45) Date of Patent: Sep. 17, 2013

(54) DEVICES FOR AND METHODS OF MONITORING A PARAMETER OF A FLUIDIC SAMPLE BY MICRODIALYSIS

(75) Inventors: Franz Feichtner, Graz (AT); Lukas Schaupp, Graz (AT); Hans Koehler, Graz (AT)

(73) Assignee: Joanneum Research Forschungsgesellschaft mbH, Graz (AT)

(*) Notice: Subject to any disclaimer, the term of this patent is extended or adjusted under 35 U.S.C. 154(b) by 663 days.

(21) Appl. No.: 12/446,234

(22) PCT Filed: Oct. 18, 2007

(86) PCT No.: PCT/EP2007/009056
§ 371 (c)(1),
(2), (4) Date: Sep. 24, 2010

(87) PCT Pub. No.: WO2008/046630
PCT Pub. Date: Apr. 24, 2008

(65) Prior Publication Data
US 2011/0011786 A1    Jan. 20, 2011

Related U.S. Application Data

(60) Provisional application No. 60/862,100, filed on Oct. 19, 2006.

(51) Int. Cl.
*B01D 61/24* (2006.01)
*B01D 61/28* (2006.01)
*B01D 69/08* (2006.01)
*B01D 63/02* (2006.01)

(52) U.S. Cl.
USPC ........... 210/645; 210/321.84; 210/500.21; 210/500.24; 210/646

(58) Field of Classification Search
USPC ............ 210/321.62, 321.75, 321.84, 500.21, 210/500.24, 645, 646
See application file for complete search history.

(56) References Cited

U.S. PATENT DOCUMENTS

| 4,786,410 A | 11/1988 | Benattar et al. |
| 4,832,034 A | 5/1989 | Pizziconi et al. |
| 6,284,115 B1 | 9/2001 | Apffel |

FOREIGN PATENT DOCUMENTS

| DE | 3806008 A1 | 8/1988 |
| DE | 19612105 A1 | 2/1997 |
| DE | 19612105 A1 | 10/1997 |
| DE | 19941271 A1 | 4/2001 |
| DE | 19941271 A1 | 5/2001 |
| EP | 2003008866 A2 | 4/1981 |
| EP | 1535636 A1 | 1/2005 |

(Continued)

OTHER PUBLICATIONS

Boubriak, et al., Monitoring of Lactate and Glucose Levels in Engineered Cartilage Construct by Microdialysis, Journal of Membrane Science 273 (2006), pp. 77-83.

(Continued)

*Primary Examiner* — John Kim
(74) *Attorney, Agent, or Firm* — Robert A. Blaha; Smith Risley Tempel Santos LLC (57) ABSTRACT

A device for monitoring a parameter of a fluidic sample by microdialysis, the device comprising a permeable membrane, wherein the permeable membrane has a first surface to be brought in contact with the fluidic sample to traverse the permeable membrane (300), wherein the permeable membrane has a second surface to be brought in contact with a dialysis fluid, and wherein the first surface is smoother than the second surface.

13 Claims, 3 Drawing Sheets

(56) References Cited

FOREIGN PATENT DOCUMENTS

| | | |
|---|---|---|
| EP | 1535636 A1 | 6/2005 |
| JP | 2005224604 A | 8/2005 |
| WO | 9425875 A1 | 11/1994 |
| WO | WO9425875 A1 | 11/1994 |
| WO | WO9929355 A1 | 6/1999 |
| WO | WO9945982 A2 | 9/1999 |
| WO | 0178805 A1 | 10/2001 |
| WO | 03003911 A2 | 1/2003 |
| WO | WO03003911 A2 | 1/2003 |
| WO | 2004056459 A1 | 7/2004 |
| WO | WO2004056459 A1 | 7/2004 |
| WO | 2008046779 A1 | 4/2008 |
| WO | 2008048183 A1 | 4/2008 |
| WO | 2009048183 A1 | 4/2009 |

OTHER PUBLICATIONS

Torto, et al., Optimal Membrane Choice for MicrodialysisSampling of Oligosaccharides, Journal of Chromatography A, 806 (1998), pp. 265-278.

DEVICES FOR AND METHODS OF MONITORING A PARAMETER OF A FLUIDIC SAMPLE BY MICRODIALYSIS

This application claims the benefit of the filing date of U.S. Provisional Patent Application No. 60/862,100 filed Oct. 19, 2006, the disclosure of which is hereby incorporated herein by reference.

The invention relates to a device for monitoring a parameter of a fluidic sample.

The invention further relates to an apparatus for monitoring a parameter of a fluidic sample.

Moreover, the invention relates to a method of monitoring a parameter of a fluidic sample.

Beyond this, the invention relates to methods of use.

Furthermore, the invention relates to a microdialysis device.

Porous membranes are used in many technical fields, including plasmafiltration, plasmapheresis, dialysis and blood oxygenation. Theses porous membranes are therefore incorporated in apparatus for therapeutic use.

US 2005/0187508 discloses an elongated hollow microporous fiber comprising an inner wall surface defining an interior fiber lumen, an outer wall surface, and a microporous fiber wall therebetween, the fiber wall having one or more continuous, cohesive, elongated filaments embedded in the fiber and extending lengthwise of the elongated fiber along substantially the full length of the fiber.

US 2005/0121384 discloses an in-vivo plasmapheresis and/or in-vivo ultrafiltration membrane which comprises elongated hollow fibers each fiber having an interior lumen extending along the fiber length, the fiber wall having a plurality of zones between the inner and outer wall surfaces, each of the zones having a mass density different than the mass density of an adjacent zone. The fiber wall is characterized by having a lower mass density zone at the inner wall surface and a higher mass density zone at the outer wall surface. The fiber is further characterized by having an average elongation breaking force strength of at least about 0.2 lbs. and an average elongation of at least about 45%.

WO 99/29355 discloses a method and an apparatus for calculating the concentration of a substance in blood of a mammal. Blood from the mammal is passed through a dialyser having a semipermeable membrane and a dialysing fluid is passed at the other side of the membrane. The concentration of urea $c_d$ is measured in the dialysate emitted from the dialyser and the dialysate fluid flow rate $Q_d$. A disturbance is introduced in the dialyser whereupon the effective dialysance Ke of the dialyser is calculated. Finally, the concentration of urea in blood is calculated by the formula $c_{pw}=c_d \times Q_d/K_e$. By using the curve of urea concentration $c_d$ versus time in the dialysate, it is possible to calculate the initial mass $m_0$ of urea in the blood. Finally, the distribution volume V of urea in the body of said mammal is calculated according to the formula $V=m_0/c_{pw}$.

EP 0,038,866 discloses a compact blood dialyzer having a low surface area of semi-permeable membrane. The dialyzer can be manufactured at relatively low cost to be provided as a pre-sterilized unit feasible for use in dialysis at home. Arterial pressure can pump the blood through the compact dialyzer unit. The blood and dialysate flow in multiple parallel channels on opposite sides of the semi-permeable membranes, with the blood being directed as wide thin films travelling against the surface of the membrane, thereby providing an efficient exposure of the flowing blood to the surface of the membrane.

U.S. Pat. No. 5,391,580 discloses a biocompatable multilayer article suitable for use in blood oxygenation. The article is made up of a microporous polypropylene tube, a permselective, water vapor impermeable, carbon dioxide and oxygen permeable, homogeneous layer directly adhered to the polypropylene tube and active heparin linked through a covalent bond to the permselective layer.

In contrast to therapeutic use of porous membranes, microdialysis is a known technique to continuously sample substances in tissue for monitoring purposes, using (semi-) permeable membranes to access substances in tissue.

U.S. Pat. No. 6,264,627 discloses a catheter to be inserted into a blood vessel and guided by said blood vessel which comprises a substantially cylindrical wall structure which defines an elongated catheter body having a proximal end and a distal end, an opening formed in said cylindrical wall structure which extends into said catheter body forming a microdialysis chamber therein having a proximal and distal end, a microdialysis membrane covering said opening such that said microdialysis chamber has at least a portion of said microdialysis membrane as part of its wall, first and second channels extending through at least a portion of said catheter body and having proximal and distal ends, a cross channel connecting one of said first or second channels to the more distal side of said microdialysis chamber and the other of said first or second channels connected to the more proximal side of said microdialysis chamber, said proximal ends of said first and second channels being connected to an external means for circulating, monitoring and analyzing a microdialysis solution passing therethrough.

DE 3806008 discloses long term monitoring of the blood level of various blood constituents. The monitoring is accomplished by capillary filtration and collection of an ultrafiltrate of blood. Filtration of the ultrafiltrate occurs through a filter composed of hollow fibers which are implanted within an interstitial body space in fluid communication with blood capillaries. The ultrafiltrate is drawn through the filter and into an ultrafiltrate collector which extends externally of the body. The collector provides a vacuum for withdrawing the ultrafiltrate and holds discrete liquid samples of the ultrafiltrate. The method and device is particularly suited for long term monitoring of blood glucose levels in diabetic patients or other blood chemical constituents in other patients.

WO 99/45982 discloses a catheter to be inserted into and guided by a blood vessel, and a method for detecting substances in the coronary sinus. The catheter comprises an elongate catheter body, having a distal end and a proximal end, and includes at least two channels. A first and second channel for microdialysis solution are connected with each other so that microdialysis solution can flow from one channel to the other. An opening, in connection with which a microdialysis membrane is arranged, is provided in the catheter body. A space in the catheter body is formed by a part of the first channel in connection with said opening and forms a microdialysis chamber. The catheter is connectable to external means for circulating and monitoring/analyzing the dialysis solution. In the method the concentration of at least one substance in a group, in a sample of a dialysis solution obtained by microdialysis of blood in the vascular system, e.g. in the coronary sinus, is measured and possibly compared with a reference concentration for the respective substance measured.

However, conventional microdialysis systems may be incapable of performing microdialysis stable over a sufficiently long period of time. Currently the longevity of certain medical implants suffers because bacteria, cells and proteins in the body gradually accumulate on the devices (known as fouling), compromising their performance and threatening patients with infections.

It is an object of the invention to enable analyzing a fluidic sample over a sufficiently long time interval.

In order to achieve the object defined above, a device for monitoring a parameter of a fluidic sample, a method of manufacturing a device for monitoring a parameter of a fluidic sample, an apparatus for monitoring a parameter of a fluidic sample, a method of monitoring a parameter of a fluidic sample, methods of use, and a microdialysis device according to the independent claims are provided.

According to an exemplary embodiment of the invention, a device for monitoring a parameter of a fluidic sample is provided, the device comprising a permeable membrane, wherein the permeable membrane has a first surface (selective layer) to be brought in contact with the fluidic sample to traverse the permeable membrane, and a second surface to be brought in contact with a fluid (perfusate/dialysate, which may be also denoted as a "dialysis fluid"), wherein the first surface is smoother than the second surface.

According to another exemplary embodiment of the invention, an apparatus for monitoring a parameter of a fluidic sample is provided, the apparatus comprising a device having the above-mentioned features, and a fluid transport unit adapted to bring the perfusate in contact with the second surface.

According to still another exemplary embodiment of the invention, a method of monitoring a parameter of a fluidic sample is provided, the method comprising bringing a first surface of a permeable membrane in contact with a fluidic sample to traverse the permeable membrane, wherein the first surface is smoother than the second surface, and bringing a second surface of the permeable membrane in contact with a dialysis fluid.

According to yet another exemplary embodiment of the invention, a method of using a device having the above-mentioned features for microdialysis, ultrafiltration and/or for monitoring an analyte concentration, particularly a glucose level, is provided.

According to another exemplary embodiment of the invention, a microdialysis device for analyzing a fluidic sample is provided, the microdialysis device comprising a permeable membrane, wherein the permeable membrane has a first surface to be brought in contact with the fluidic sample to traverse the permeable membrane, wherein the permeable membrane has a second surface to be brought in contact with a dialysis fluid, and wherein the permeable membrane comprises pores having a mean size which increases from the first surface towards the second surface.

According to still another exemplary embodiment of the invention, an ultrafiltration device for analyzing a fluidic sample to obtain an ultrafiltrate is provided, the ultrafiltration device comprising a permeable membrane, wherein the permeable membrane has a first surface to be brought in contact with the fluidic sample to traverse the permeable membrane, wherein the permeable membrane has a second surface to be brought in contact with the ultrafiltrate, and wherein the permeable membrane comprises pores having a mean size which increases from the first surface towards the second surface.

In the context of this application, the term "membrane" may particularly denote a thin (for instance planar or cylindrical) structure or material that separates two phases or environments. Membranes may selectively control mass transport between the phases or environments, since they may be permeable for a first group of materials and impermeable for a second group of materials.

The term "permeable" may particularly denote a material property of the membrane, namely that the membrane can be traversed—in a significant manner or quantity—by fluidic or solid particles having specific sizes. For instance, a dialysis membrane may be permeable for substances being smaller than a cut-off size of the membrane, but being impermeable for substances being larger than a cut-off size of the membrane. The term "permeable" may also cover semi-permeable or partially permeable membranes, that is to say membranes being permeable only for specific particles, whereas being impermeable for other particles, depending on properties of the membrane and the particles (like dimension, chemical properties, etc.).

The term "pores" may particularly denote any voids or holes in a wall or portions of a wall in which wall material is locally lacking. Such pores within the membrane may provide fluidic paths which allow materials having sizes which are smaller than the pores to diffuse through the pores and therefore equilibrate concentrations between an exterior and an interior of the membrane partially or fully. Such pores may be found in a sintered material or in an extruded material. Foams or the like may have such a pore structure as well.

The term "pore size", in this connection, may denote a size of the aforementioned pores. A measure for an average pore size may be given in nano/micro/milli-meters. An analogous measure of the pore size may be given in a molecular weight cut off, which may denote a limit beyond which molecules are increasingly less alike to pass through. A further analogous measure of the pore size may represent a mass density of a porous wall. The pore size is usually smaller the larger the mass density is. In an asymmetric wall structure for example, that is to say in a porous wall in which a pore size gradient is present, the pore size and accordingly the mass density may vary along a thickness of the wall. The pore size may also have an impact on the surface smoothness/roughness of the wall. Usually, small pores size and small port densities (=high mass densities) result in a smoother surface than large pores sizes and large pore densities, while large pore sizes and high pore densities (=low mass densities) result in a rougher surface than small pore sizes and small pore densities. An exemplary embodiment of the invention comprises pores having a mean size which increases from one surface of the membrane towards another surface of the membrane.

The term "mass density", in this connection, may denote a property of the material to have constant or variable density along/across its wall, thereby forming volume elements with high and/or low mass densities and accordingly low and/or high voids or pore sizes. Additionally, the term "mass density" may also represent the material's "surface smoothness/ roughness", giving a rough surface in volume elements with low mass density and giving a smooth surface in volume-elements with high mass density.

The term "surface smoothness/roughness" may denote a property of the material's surface to be smooth or rough. An adequate "surface smoothness/roughness" may be the achieved by adopting the materials "mass density" at the surface, but also mechanical (e.g. polishing, . . . ) or chemical surface modifications as well as surface coatings may yield in an adequate modification of the "surface smoothness/roughness". Such a "surface smoothness" may limit or prevent cell adhesion to the surface, pore occlusion or may enhance laminar flow of a liquid passing by, whereas "surface roughness" may enhance or promote turbulent flow of a liquid passing by.

The term "hydraulic permeability", in this connection, may denote a property of the material to allow more or less convective mass transport across the material's wall. The higher the "hydraulic permeability" the higher is the convective mass transfer across the material's wall. Low "hydraulic permeability" consequently means lower convective mass transport and higher diffusive transport across the material's wall.

In this connection, the application of membranes with a special "hydraulic permeability" may be used to differentiate "high-flux membrane applications" and "low-flux membrane applications": while "high-flux membrane applications" like common in dialysis and plasmaseperation technologies or the like yield in purifying the sampling fluid, "low-flux membrane applications" like microdialysis or ultrafiltration which are the scope of this invention yield in a partial or full equilibration of the sampling fluid with the dialysis fluid for monitoring purposes.

The term "fluidic sample" may particularly denote any subset of the phases of matter. Such fluids may include liquids, gases, plasmas and, to some extent, solids, as well as mixtures thereof. Examples for fluidic samples are blood, interstitial fluid in subcutaneous tissue, muscle or brain tissue urine or other body fluids. However, in industrial applications or in process technology applications, the term "fluidic sample" may particularly denote any fluid which may be analyzed or treated with a membrane.

The term "dialysis fluid" may particularly denote a fluid (like a buffer, water, etc.) which may be brought in interaction with the fluidic sample via the permeable membrane so that a material transport from the fluidic sample to the dialysis fluid may allow to analyze a component of the fluidic sample by analyzing the perfusate. The term "dialysis fluid" may represent the terms "perfusate" and "dialysate", which may denote the liquid entering and leaving the permeable membrane, respectively.

The term "Relative Recovery" may particularly denote one parameter that characterizes the dialysis efficiency of a microdialysis/ultrafiltration device. It may be defined as the ratio between the concentration of the analyte of interest in the dialysis fluid and the concentration of this analyte in the fluidic sample. The recovery may be given in percent.

Besides well known factors that influence the recovery like temperature, perfusate composition (differences in osmotic values of perfusate and periprobe fluid), perfusate flow rate, characteristics of the membrane, probe geometry, diffusive surface area and analyte diffusion coefficient also the surface of the membrane itself may influence the recovery.

The term "functionalize" may denote any of the following surface and/or morphology treatments:
surface activation
surface deposition
adaptation of pore size
adaptation of the surface smoothness/roughness
adaptation of the mass density
adaptation of the hydraulic permeability
adaptation of mechanical properties of the membrane
adaptation of chemical properties of the membrane (e.g. labelling amino acids, free radicals, etc.)
adaptation of surface charge (i.e. enabling to provide a positive, negative or neutral surface charge property at the membrane surface, for instance for selectively attracting or repelling specific molecules; this may allow to maintain the membrane surface free of specific molecules or to accumulate specific molecules at the surface)
for the purpose of improving the quality and the performance of a monitoring device (like a microdialysis or ultrafiltration probe).

"Functionalization" in this connection may denote surface and/or morphology treatments which in general enhance or promote a capability of the surface and/or morphology to fulfill an assigned function, like its mechanical stability, suppression of fouling, pore occlusion or bacterial growth, the maintenance of stable analyte recovery as well as the reduction of risks associated with the use of such probes in living organisms, like coagulation, inflammation and rejection reactions.

The term "surface activation" may denote the introduction of chemical functional groups (like heparin) to a surface. "Surface activation" may include at least one of the following techniques comprising anti-bacterial, anti-coagulational, anti-inflammational, anti-adhesive surface treatments.

The term "surface deposition" may denote any kind of material deposition (for instance formation of a layer (being active, like a heparin layer, or passive, like a Teflon layer) or material immobilization).

The term "ultrafiltration" may particularly denote a variety of membrane filtration in which hydrostatic pressure forces a liquid against a (semi-)permeable membrane. Suspended solids and solutes of high molecular weight are retained, while water and low molecular weight solutes pass through the membrane.

In the herein enclosed embodiments, ultrafiltration may be meant to be used for monitoring purposes.

The term "microdialysis" may particularly denote a method which is mainly based on diffusion. It may be used for monitoring analyte concentrations, wherein two phases are separated by a (semi-)permeable membrane. A first phase may be a milieu to be investigated by monitoring the concentration of one or several analytes. A second phase may be a liquid phase into which analytes diffuse and equilibrate partially or fully with the first phase, without systemically altering the concentration of the analyte in the first phase. In particular, at least the second phase may be transported with flow rates in the range between 0.1 and 1000 μl/min.

The term "structure" may denote any piece of material. It may be a one-dimensional structure, a planar structure, a three-dimensional structure, etc. Examples are tubes, rectangles, circles, polygones.

The term "flexible" may particularly denote a material property of the membrane, namely that the membrane can be reversibly deformed under the influence of an external force.

The term "biocompatible" may particularly denote a material property of the membrane, namely that the membrane, when inserted in living tissue, does not harm or negatively influence the physiological conditions at such a location in a body.

The term "physiological object" may particularly denote any (living or dead) organism, like a human being, an animal, or a plant (any organism).

The term "physiological parameter" may particularly denote any parameter which is related to the physiology of a living organism, for instance the metabolism, etc. Such a physiological parameter may include the concentration of an exogenous or endogenous marker, a protein concentration, etc.

The term "physiologically active substance" may particularly denote any substance which may have an effect on the physiology of the living organism, for instance a medication, a drug, etc.

The term "monitoring" may denote a continuous or discontinuous measurement of an analyte concentration in the object of investigation. It may include comparing a measured analyte concentration with the true systemic concentration in the object of investigation.

During monitoring, sensors may be used. Appropriate monitoring may require that a membrane used in the context of monitoring does not allow specific (particularly very large)

molecules to traverse the membrane. Such specific (particularly very large) molecules might deteriorate a sensor surface and might make monitoring impossible. Particularly, sensors may be very sensitive with regard to large proteins (which occur in blood, for instance) so that a membrane suitable for monitoring should be impermeable for such large protein molecules.

The term "smoother" may denote that a surface roughness of a smoother surface is smaller than a surface roughness of another (rougher) surface. The quality of technical surfaces (a measure for irregularities) may be characterized by the term "roughness". The following roughness measurement quantities are determined according to DIN 4768: the centerline average height (Ra) is the arithmetic mean value of all distances of the profile from the centerline. The averaged depth of roughness (Rz) represents the arithmetic mean from the individual depths of roughness of five subsequent individual lines. A roughness of the first and the second surface may be compared based on these parameters.

According to an exemplary embodiment of the invention, a membrane may be provided having a first smooth surface to be brought in contact with a fluidic sample like blood and having a second rough surface to be brought in contact with a dialysis fluid like an aqueous buffer. The smoothness of the first surface may result in an effect that proteins or other macromolecules of the fluidic sample are prevented from traversing the membrane or from accumulating in pores at or close to the first surface. Simultaneously, the roughness of the second surface may result in an effect that a turbulent flow of the dialysis fluid occurs due to mechanical irregularities at or close to the second surface. This may promote substance exchange via the membrane, thereby yielding an improved recovery. The first surface may be smooth in order to reduce or prevent the risk of fouling and/or cell adhesion to the surface or pore occlusion or to increase the likelihood to have laminar flow conditions for liquids passing by.

In the following, some properties of a membrane according to an exemplary embodiment of the invention will be summarised, and corresponding advantages obtainable when implementing such a membrane in a monitoring device.

A smooth surface characteristic of the membrane on the surface being in contact with the fluidic sample (for instance blood) may ensure a proper performance of the device, namely a long-time stability of the recovery, an anti-fouling feature, and an anti-coagulation feature. Furthermore, implementing such a device into a body of a patient may ensure anti-coagulation, anti-fouling, biocompatibility and improved thrombogenity properties.

A (relatively) smooth (not too rough) surface on the side of the dialysis fluid (that is to say the side of the perfusate) may improve the performance of the device, since adhering substances may be prevented from adhering to such a membrane. Furthermore, the estimation of the true concentration of a substance may be more accurate.

However, a relatively rough surface on the side of the membrane being in contact with the dialysate (the perfusate side) may improve the performance of the device, since a turbulent flow may be promoted on the side of the perfusate. This may result in a better distribution of the analyte in the solution, and thus a higher recovery.

The adjustment of (for instance variable) pore sizes may further improve the performance of the device. This parameter may allow to adjust the cut-off for specific sizes of molecules. The pore size may be in the order of magnitude of nanometers. This may prevent plasma proteins to traverse the membrane, which may be highly advantageous for an online evaluation of sensor measurements. However, the pore size may also be in the micrometer region. This may promote a material exchange via the membrane and may prevent blocking of channels of the membrane. A sufficiently large pore size may prevent a reduction of the recovery.

The molecular weight cut off of the membrane may be adjusted to improve the performance of the device, since this parameter may determine a limit for substances capable of traversing the membrane. A proper value of the molecular weight cut off may be in the region between 1 kDa and 100 kDa, particularly between 5 kDa and 10 kDa.

The mass density of the membrane may be a further parameter which may be adjusted in order to improve the performance of the device.

Also the hydraulic permeability may have an influence on the performance of the device. Embodiments of the invention may intend specifically to have an equilibrium between an outside and an inside of the membrane, so that the adjustment of the hydraulic permeability may make the membrane specifically appropriate for monitoring applications.

Mechanical stability of the membrane may also be an important parameter, since this may prevent that the membrane is mechanically destroyed, allows to bear a high mechanical stress when inserting or removing the membrane into or from a body, and may ensure to bear a larger stress during the operation of the device. This may also guarantee a patient to use the device in a secure manner, since the risk of thrombosis and infarcts may be reduced.

Furthermore, different kinds of functionalisations may improve the performance.

A functionalisation by immobilizing amino acids and/or free radicals, enzymes, etc. on the membrane may be advantageous.

Moreover, an anti-coagulation coating (for instance a heparinization), particularly on a side of the membrane which is brought in contact with the fluidic sample (for instance blood) may be advantageous for the performance of the device to suppress fouling and to make recovery more stable. With regard to the security of a patient, this may reduce the danger of coagulation and thrombogenity.

An anti-inflammatory coating, particularly on the side of the membrane being in contact with the fluidic sample (for instance blood) may improve the safety of a patient, since inflammatory reactions may be suppressed and an improved biocompatibility may be achieved. With regard to the performance of the device, this may reduce the influence of the membrane onto a substance to be analysed (for example when inflammation markers shall be measured, but a conventional device may generate by its own inflammation).

An anti-bacterial coating, particularly on the side of the membrane being brought in contact with the fluidic sample (for instance blood) may improve the safety of a patient, since a bacterial growth and therefore an inflammation may be suppressed. Furthermore, any influence of such a fact to the analyte concentration (bacteria may consume glucose) may be suppressed by such a measure.

An anti-adhering coating particularly on the side of the membrane being brought in contact with the fluidic sample (for instance blood) may improve the performance of the device with regard to long-term stability of the recovery, an anti-fouling feature, and an anti-coagulation feature. With regard to a safety of a patient, this may have a desired impact on anti-coagulation, anti-fouling, an improved biocompatibility and an improved thrombogenity.

An anti-adhering coating on the side of the dialysis fluid (that is to say on the perfusate side) of the membrane may improve the performance of the device, since, for instance for measuring adhering substances, these do not stick between the body and the sensor, and this may allow to measure a concentration in an improved manner.

According to an exemplary embodiment of the invention, a membrane may be provided having an activated surface which can be brought in contact with a fluidic sample (for instance blood) to be analyzed. The surface to be brought in contact with the fluidic sample may have such a functionalization (for instance may be heparinized) that the permeability of the permeable membrane is not negatively influenced by components of the fluidic sample, for instance blood plasma or large proteins or by reactive processes inside the object of investigation resulting in an encapsulation, isolation or rejection. Therefore, in case of a tubular membrane, an outer surface may be selectively functionalized. When the outer surface is then brought in contact with the fluidic sample, the functionalization avoids undesired accumulation of large molecules of the fluidic sample at the membrane which might negatively influence permeability of the membrane. The inner surface may be free of a functionalization, since the inner surface is intended to be contacted with a freely selectable dialysis fluid. Via the permeable membrane, components of the fluidic sample diffusing through the membrane may be introduced in the dialysis fluid flowing along the inner surface. Consequently, concentrations of components in the perfusate after being brought in interaction with the fluidic sample may be a fingerprint of the corresponding concentrations of these components in the fluidic sample. When analyzing components of the dialysis fluid after an at least partial equilibration with the fluidic sample, information regarding the fluidic sample may be derived, for instance a glucose concentration in the fluidic sample.

As an alternative to the previously described embodiment, it is also possible that both surfaces of the membrane are functionalized. For example, it is possible to analyze the concentration of a substance which has an adhering property. By an adequate coating also on an inner surface of a (tubular) membrane and the route to the sensor, it may be possible to prevent the substance from adhering at the inner surface. Thus, a secure transport of the sample to a sensor may be guaranteed. Such anti-adhesive coatings may include silicones and flouro-polymers. The company Accelr8-Technology Corporation for example provides the Opti-Chem Bio-Coatings which have the ability to prevent or delay non-specific adsorption of bio-materials to surfaces.

In addition to the functionalization of the first surface, a pore structure of the permeable membrane may be adjusted to further suppress fouling and occlusion of the membrane. Namely, pores at the functionalized first surface may be made smaller than pores at the second surface. In other words, the membrane may be formed to have a mean pore size gradient between a first surface and a second surface. Such an asymmetric wall structure (similarly as in case of US 2005/0187508) may be found in a membrane in which an outer surface of the membrane has a structure having a higher mass density than an inner surface of the membrane. This may avoid that large molecules of the fluidic sample accumulate in the pores, since the pores may be made smaller than the size of such large molecules. Particularly the combination of a functionalization of the fluidic sample contacting surface and a provision of this surface with a sufficiently small average diameter of the pores may allow for a long-term stable maintenance of the transmissibility of the membrane.

With regard to membranes having a pore size varying along of a thickness of the membrane, it may possible to employ membranes as disclosed in US 2005/0187508, US 2006/0124530, US 2005/121384, or U.S. Pat. No. 6,802,971 according to exemplary embodiments of the invention.

Regarding the use of such membranes in the context of exemplary embodiments of the invention, explicit reference is made to the disclosure of these documents related to membranes having a pore size varying along a thickness of the membrane and to methods of manufacturing such membranes. Particularly, the skilled person will clearly understand that the use of other materials or the manufacture of membranes having pore sizes of other dimensions and having further alternative properties will become possible by varying process parameters (like pressure, temperature, material composition, etc.) of the manufacture procedures of the membranes described in US 2005/0187508, US 2006/0124530, US 2005/121384, or U.S. Pat. No. 6,802,971.

Therefore, particularly for applications in the field of microdialysis and ultrafiltration, a secure, reliable and easily manufacturable device may be provided which is particularly appropriate for long-term applications, for instance as a catheter for monitoring the glucose level of an intensive care patient over 72 hours or more.

Such a device may be integrated in an apparatus for analyzing a fluidic sample, e.g. for monitoring the glucose level of an intensive care patient. Investigations have shown that the monitoring and correct adjustment of the glucose level of intensive care patients may significantly reduce the risk of morbidity and mortality of these patients. Therefore, the device for analyzing a fluidic sample according to an exemplary embodiment may be used to estimate the glucose level and, if desired, supply medication or other physiologically active substances (for instance glucose and/or insulin) to the patient so as to adjust this parameter.

Another exemplary field of applications are pharmacological investigations, related to the development and test of medications or drugs.

Therefore, embodiments of the invention may make it possible to determine the free concentration of substances or drugs in the body of a human being using a membrane with a functionalized surface. For example, medication may be selectively bound to an outer surface of a tubular membrane. In order to avoid undesired effects like fouling or coagulation, the surface which is brought in interaction with the fluidic sample (like blood) may be made smoother than the other surface.

Embodiments of the invention may allow to regulate the glucose level of intensive care patients in an automated manner. For this purpose, the glucose level may be measured in subcutaneous fat tissue or, which may be preferred, in blood. An investigation of the subcutaneous fat tissue has the advantage that the interstitial fluid located there is less likely to respond in physiological reactions like encapsulation, isolation or rejection than blood (for instance with regard to fouling or the blood coagulation cascade). However, using blood has the advantage that it allows to measure for example the free systemic concentration of physiological parameters (like glucose level) in a highly accurate manner. However, when blood shall be used as a fluidic sample, there is the danger that components of the blood may cover the permeable membrane and may deteriorate its permeability. In order to reduce or eliminate such problems, the concept of a conventional dialysis membrane is inverted by embodiments of the invention so that an outer surface of a tubular membrane may be functionalized according to the above given definition. Examples for such a functionalization include surface modifications of the membrane with regard to the pore structure across the membrane wall, where the outer surface of the membrane may be smoother (=higher mass density=smaller pore size) compared to the inner surface. Other forms of functionalisation may include a heparinization in order to prevent or suppress coagulation, an antimicrobial deposition (for instance using silver or copper) in order to prevent or suppress bacterial reactions, or an anti-inflammatory deposition in order to prevent or suppress physiological responses resulting from probe implantation, or also anti-adhesive coatings in order to prevent or suppress the deposition of biological materials or drugs, or even morphological adoptions in order to increase the probes mechanical stability.

For example, in vascular microdialysis, the stability of the measurement accuracy may be ensured over periods of time of much larger than 24 hours, particularly 72 hours, even 96 hours or 5 to 6 days. These are typical periods for which a person is on an intensive care station.

According to an exemplary embodiment of the invention, the dimension of pores of the permeable membrane may be adjusted such that the average pore size is larger at the surface to be brought in contact with the dialysis fluid than at a surface to be brought in contact with the fluidic sample. This may prevent large molecules (which may be present in a fluidic sample like blood) from diffusing into the pores to occlude them. It is possible that an average pore size is increased continuously from the first surface to the second surface, for instance by modifying a pore size determining parameter during manufacture. It is also possible that an average pore size is increased stepwise from the first surface to the second surface, for instance by manufacturing a plurality of layers deposed on one another, each layer having a specific pore size. Thus, a pore size design in accordance with a specific application is possible.

The membrane may be made of a hydrophilic material so that liquid components of the fluidic sample and the dialysis fluid may have the tendency to be present in the pores of the membrane and thereby reducing the effective diffusion distance between the outer and the inner surface resulting in a better diffusion behaviour. The membrane may also be made of a lipophilic material so that lipids may traverse the membrane if certain lipids or lipophilic substances have to be monitored. Furthermore, the material of the membrane may be robust and flexible so as to be appropriate for implantation, for instance using catheters.

Exemplary embodiments of the invention may be used in the field of microdialysis, particularly for blood microdialysis. In contrast to conventional microdialysis membranes in which components of the blood may foul or occlude the pores of the permeable membrane which may have an influence on the recovery rate, embodiments of the invention provide a microdialysis membrane with a stable recovery rate by functionalization of a membrane surface which is located towards a body fluid, for instance an outer surface of a tubular membrane. This may be combined advantageously with the provision of a spatially dependent pore size distribution along a thickness of the membrane, thereby enabling proper transmission properties and a protection against pore occlusion.

Exemplary embodiments of the invention provide a microdialysis membrane which may be used in the field of microdialysis to promote a partial exchange of low-molecular substances driven by diffusion. Exemplary embodiments do not intend to provide for a therapy, but in contrast to this for continuously monitoring a concentration of a substance in a body. Particularly, embodiments of the invention may tend to establish an equilibrium between both surfaces of a membrane.

Next, further exemplary embodiments of the device for monitoring a parameter of a fluidic sample will be explained. However, these embodiments also apply to the apparatus, and to the methods.

The permeable membrane may comprise a hollow tube. An outer surface of the hollow tube may form the first surface, and an inner surface of the hollow tube may form the second surface. In such a configuration, a tubular membrane is provided which may be implanted for example in an artery, a vein or any other tissue of a patient. An outer surface of the hollow tube may be brought in contact with a body fluid like interstitial fluid or blood, wherein the dialysis fluid may flow through the channel formed within the hollow tube. Such a configuration may be suitable for an intracorporeal analysis or for an extracorporeal analysis.

Alternatively, the permeable membrane may comprise a planar structure. In such a configuration, the fluidic sample may be brought in contact with one main surface of the planar structure (for instance a circular or rectangular sheet), whereas the other main surface may be brought in contact with the dialysis fluid. Diffusion may then occur through the planar membrane. Such a configuration may be particularly suitable for an extracorporeal analysis.

The first surface and the second surface may be located at opposing sides of the permeable membrane. In other words, the membrane may separate the two surfaces so that fluid communication between the two surfaces is mediated via the membrane.

The permeable membrane may comprise pores. The mean size of the pores may increase from the first surface towards the second surface. In other words, the pore size may increase (in a continuous or discontinuous manner) from a surface facing the fluidic sample to a surface facing the dialysis fluid, thereby reducing the probability that pores are occluded by big molecules of the fluidic sample.

The pores may have a size at the first surface in the range between essentially 0.3 µm and essentially 1.0 µm, particularly in the range between essentially 0.4 µm and essentially 0.8 µm. The pores may have a size at the second surface in the range between essentially 1.0 µm and essentially 60 µm, particularly in the range between essentially 2 µm and essentially 6 µm. Membranes having such pores are disclosed, as such, in US 2005/018708 A1.

Alternatively, the pores may have a size at the first surface smaller than essentially 0.1 µm, particularly in the range between essentially 0.05 µm and essentially 0.09 µm. The pores may have a size at the second surface larger than essentially 0.1 µm, particularly in the range between essentially 0.1 µm and essentially 0.4 µm. Such a membrane may be prepared by extrusion from a blend of polyethersulfone and polyvinylpyrrolidone. Other materials may be used as well, like Cellulose, Copolymer (polyacetronitrile/sodium methallyl sulfonate), Copolymer (polycarbonate/polyether), Acrylic copolymer, Polysulfone, Cuprophane, Polyarylethersulphone (PAES), Polyethersylfone (PES), Polycarbonate (PC), and/or PAN. Still other possible membrane materials may include inorganic materials like Ceramic, Glass, Stainless steel or derivatized carbon.

With such a membrane, large components of blood (for instance solid components like erythrocytes) may be prevented from entering the membrane at the first surface. At the same time, proper transmission properties may be ensured, allowing the membrane to be used for microdialysis applications or the like.

The selectivity of the membrane can also be expressed in terms of its molecular weight cut-off (MWCO). Molecules having a higher molecular weight than the MWCO will not be able to pass the membrane. Typical values are between 1 kDa and 100 kDa, particularly between 5 kDa and 50 kDa, more particularly 10 kDa.

The first surface may be smoother than the second surface. The smooth surface may further suppress deposition and activation of large compounds of the fluidic sample at the first surface.

The permeable membrane may be permeable only for materials which do not exceed a threshold size. In other words, the pores in the permeable membrane may be dimensioned in such a manner that desired molecules (for instance glucose molecules) can traverse the permeable membrane, whereas large molecules like erythrocytes or large proteins may be kept outside the permeable membrane. Therefore, by adjusting a molecular weight cut-off (MWCO) for molecule sizes which are still capable of traversing the permeable membrane may allow to adjust the functionality of the device. Examples for such a threshold size are 5 kDa or 20 kDa or a MWCO of up to 100 kDa. The permeable membrane may be made of a biocompatible material (so that it may be appropriate to be inserted into a patient's body). Particularly, such a biocompatible material shall be configured in such a manner so as to allow for in vivo or at least in vitro experiments.

The permeable membrane may be made of a hydrophilic material, that is a material having an affinity for water or having a strong attraction to water. This may allow fluidic components of the fluidic sample and/or dialysis fluid to fill the pores of the permeable membrane, thereby supporting or promoting a proper material exchange via the membrane.

The membrane may also be made of a lipophilic material so that lipids may traverse the membrane if certain lipids have to be monitored.

The permeable membrane may also be made of a flexible material, thereby allowing the device to be adjusted to anatomical conditions within a patient's body, without being injured or without injuring the surrounding material, like tissue in a blood vessel.

The first surface may be adapted to be brought in contact with blood to partially traverse the permeable membrane when analyzing the fluidic sample. In order to be able to operate at a stable level of analyte recovery in blood which is relatively "aggressive", a corresponding probe functionalization may be performed.

The second surface may be free of a functionalization or may be functionalized. The selection of the dialysis fluid is relatively free, so that it can be selected in such a manner that no fouling or occlusions occur at the second surface. Therefore, the device may be manufactured with low effort when such a functionalization is only necessary at the first surface. However, according to exemplary embodiments, also the second surface may be functionalized, for example in an identical or varying manner like the first surface.

The first surface may be functionalized in a manner to suppress deposition and activation of components of the fluidic sample on the first surface (fouling). For example, by providing the first surface with heparin, it may be prevented that blood coagulation occurs and that consequently large solid components of blood accumulate on the first surface and occlude membrane pores. Taking this measure may allow to maintain the permeability of the membrane. Heparin is a drug which may be given intravenously which thins the blood when there is danger of clotting (an anticoagulant).

The first surface may be functionalized by a functional customization for use in special tissues or organs, by a heparinization, by an antimicrobial functionalization, by an antibacterial functionalization, by an anti-inflammational functionalization, by an anti-coagulational functionalization and/or by an anti-adhesive functionalization. In other words, the specific way of functionalizing the surface may strongly depend on the specific application, having the purpose to prepare the surface appropriately for an application in a specific environment and/or to maintain the function of the permeable function of the membrane.

The first surface may be functionalized by depositing an anti-adhesive coating, for instance using silicones or flouropolymers.

The hydraulic permeability may also serve as a measure for a membrane pore size. The term "hydraulic permeability" (correlated with hydraulic conductivity) may particularly denote a measure of the ability of a material to transmit fluids. The flow of water through a porous media may be defined by the term hydraulic conductivity which is a property of the porous media only, not the fluid, and describes the ease with which water can move through pore spaces or fractures.

The device may be adapted for microdialysis, particularly vascular microdialysis. The device may also be adapted for filtration, particularly ultrafiltration. However, any other fields of application are possible as well.

The device may be adapted as an implant for being (removably) implanted into a physiological object, particularly into a blood vessel of a human being or an animal. Therefore, the device may also be suitable for medical applications in human beings or animals.

In the following, further exemplary embodiments of the apparatus will be explained. However, these embodiments also apply to the device and to the methods.

The fluid transport unit (for instance a pump or any fluid transport mechanism) may also be adapted to bring the fluidic sample and the dialysis fluid in contact with the first and the second surface, respectively. Therefore, a mechanism may be provided to transport the fluidic sample and the dialysis fluid to the corresponding one of the opposing surface portions of the flexible membrane.

According to an exemplary embodiment, the apparatus may comprise a first substrate (like a cuboid plastic body) having a first fluidic path (for instance manufactured by milling a surface of the cuboid plastic body) through which the dialysis fluid is guidable. Such a fluidic path may be a channel formed in a surface portion of the first substrate. Correspondingly, an accordingly designed second substrate may be provided having a second fluid path through which the fluidic sample is guidable. The first substrate and the second substrate are mountable in such a manner that the first substrate and the second substrate sandwich the membrane device. In other words, the membrane may be positioned between the first substrate and the second substrate, and the first and the second fluid paths may be partially or entirely matched to one another (for instance may be shaped correspondingly). In other words, the fluidic sample flows through the second fluidic path, and the dialysis fluid flows through the first fluidic path. Since the membrane is positioned in functional contact with both fluids, material transfer along the fluidic path may be enabled through the membrane. This allows for an extracorporeal and accurate analysis.

The first fluidic path and/or the second fluidic path may be shaped in a meandrous shape, a spiral shape, in a zig-zag shape, or in any other fluid path elongating manner. By such configurations, the effective length of the fluidic paths may be extended, allowing a miniature apparatus and an efficient material transfer.

A tubular (for instance cylindrical) membrane may be used as a (temporary) implant in a body (e.g. blood, muscle, fatty tissue) of a physiological object (e.g. human, animal, plant). Through an inner lumen of the membrane, a perfusate/dialysis fluid may be conducted. Via the (semi-)permeable membrane, an at least partial equilibration occurs. This may allow to monitor a physiological parameter (like a concentration of glucose in blood), in an intracorporeal embodiment.

The apparatus may further comprise a sensor adapted for sensing a physiological parameter in the dialysis fluid after being brought in interaction with the fluidic sample. Such sensors are known, as such, in the related art, and allow to determine the value of a physiological parameter, for instance of a glucose concentration in blood, by analyzing the dialysis fluid after being brought in contact with blood.

Beyond this, an infusion unit may be provided and adapted for administering a physiologically active substance (for instance glucose and/or insulin) into an object under examination (for instance a patient) in a quantity which may be determined based on a sensed value of the physiological parameter. For example, when it has been determined that the glucose concentration is not in a desired range, the glucose concentration may be selectively increased or decreased by the administration of a corresponding amount of medication. Particularly, taking such a measure may allow to significantly reduce the mortality of an intensive care patient.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

The illustration in the drawing is schematically. In different drawings, similar or identical elements are provided with the same reference signs.

In the following, referring to FIG. 1, a device 100 for analyzing a sampling fluid according to an exemplary embodiment of the invention will be explained.

The device 100 comprises a permeable membrane 101 which is shaped as a hollow tube. An outer surface 102 of the hollow tube 101 is brought in direct contact with a sampling fluid 103 in an object of investigation. Sufficiently small components of the sampling fluid 103 may traverse the permeable membrane 101 during microdialysis or ultrafiltration.

The permeable membrane 102 furthermore has a second, inner surface 104 adapted to be brought in contact with a dialysis fluid indicated schematically with reference numeral 105. The dialysis fluid 105 may be pumped through the hollow channel of the permeable tubular membrane 101, and can be selectively brought in interaction with components of the sampling fluid 103 diffusing through the permeable membrane 101, as indicated schematically by double arrows 106.

The outer surface 102 (=selective layer) is functionalized, e.g. by heparinization, that is to say by binding heparin to the outer surface 102. Heparin may prevent coagulation of blood (=sampling fluid) 103 to maintain permeability of the permeable membrane 101 when analyzing the blood (=sampling fluid) 103. Therefore, the heparin material deposited on top of the outer surface 102 prevents coagulation or deposition of large molecules of the blood (=sampling fluid) 103 on top of the outer surface 102.

A length L of the device 100 may be between 1 mm and 70 mm, particularly 20 mm. An inner diameter $d_1$ of the device 100 may be between 0.1 mm and 1 mm. An outer diameter $d_2$ of the device 100 may be between 0.2 mm and 5 mm.

Figure 1:
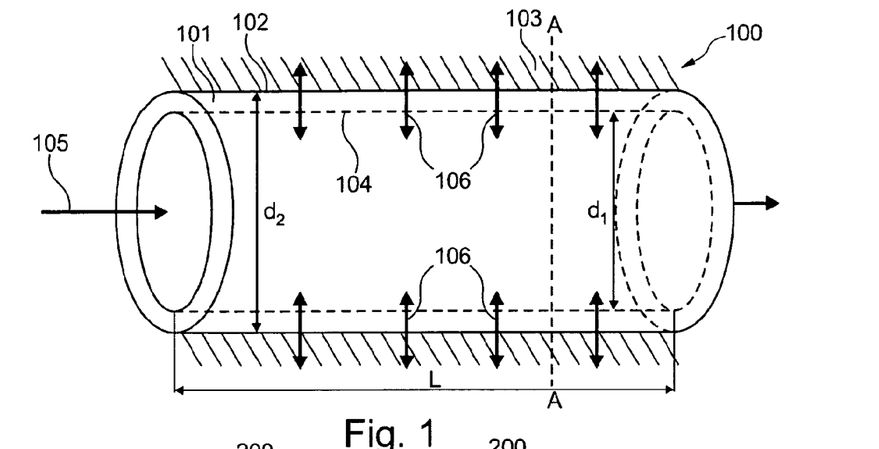
FIG. 1 to FIG. 6 show devices according to exemplary embodiments of the invention.
Figure 2:
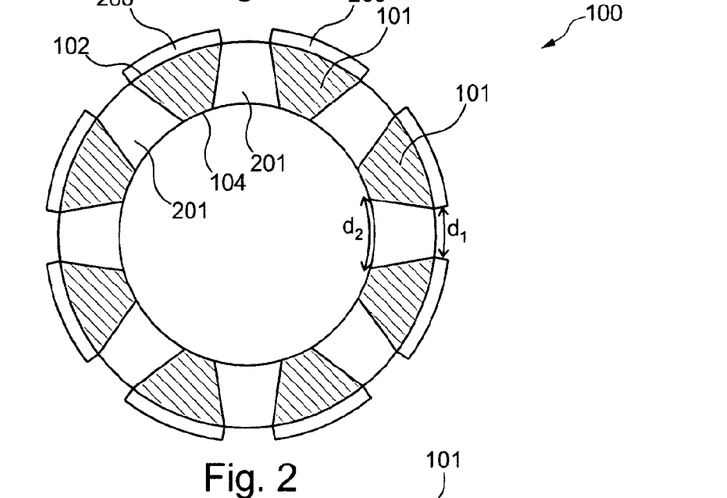

FIG. 2 shows a cross-sectional view of the device 100 along a line A-A as shown in FIG. 1.

The cross-sectional view of the device 100 is highly schematic and illustrates only the general concept of the described embodiment. As can be taken from FIG. 2, a functionalization layer 200 is provided on top of the outer surface 102 (=selective layer), thereby providing the above described functional attributes. Still another form of functionalization is to adjust the permeability of the membrane 101 in such a manner that an average pore size $d_1$ at the outer surface 102 of the device 100 is smaller than an average pore size $d_2$ at the inner surface 104.

It is emphasized that the illustration in FIG. 2 is highly schematic. In a more realistic description or illustration, an increasing average pore size from the outer surface 102 to the inner surface 104 occurs (see FIG. 9).

Beyond this, the outer surface 102 is smoother than the inner surface 104. That is to say, a higher surface quality or lower surface roughness is present at the outer surface 102 compared to the inner surface 104.

This surface smoothness may represent the higher mass density (=lower pore size) of the outer surface 102 compared to the inner surface 104.

The permeable membrane 101 is permeable only for particles which do not exceed a threshold value, which depends on the smallest pore size $d_1$. This may allow to prevent large components of the sampling fluid 102 from entering the pores 201, so that the danger of fouling or occlusion of the pores 201 is significantly reduced.

The permeable membrane 101 is further made of a hydrophilic and flexible material.

The permeable membrane 101 may also be made of a lipophilic material and flexible material so that lipids may traverse the membrane easily, if certain lipids or other lipophilic materials have to be monitored.

As can be taken from FIG. 2, the inner surface 104 is free of any functionalization, in the present embodiment free of any heparinization. In an alternative embodiment, not only the outer surface 102, but also the inner surface 104 may be functionalized, for instance may be coated with an anti-adhesive coating.

The device 100 is adapted to be implanted in an artery or a vein of a patient and may stay there for, for instance, 72 hours. By the material equilibration via the membrane 101, concentrations of components of the sampling fluid 103, for instance a glucose level, can be monitored by analyzing the dialysed perfusate 105 with a corresponding sensor in fluid communication with the dialysed perfusate 105.

Figure 3:
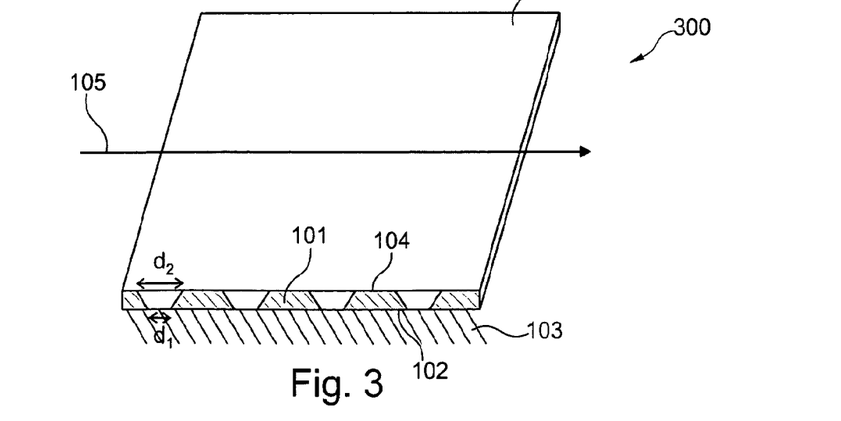

FIG. 3 shows a device 300 according to an exemplary embodiment of the invention.

The device 300 differs from the device 100 in that the permeable membrane 101 has a planar structure in FIG. 3, for instance a sheet-like structure.

Figure 4:
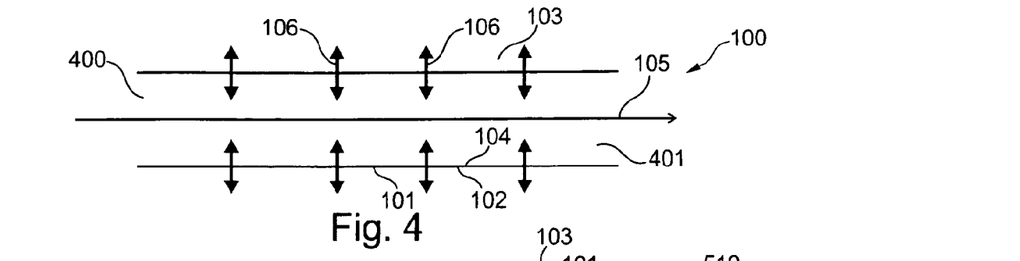

FIG. 4 shows a longitudinal section of a tubular device 100 in a so-called linear geometry.

The perfusate 105 (which may also be denoted as a dialysis fluid) is directed in a longitudinal direction through the hollow tube 101 having an inlet opening 400 and an outlet opening 401.

Figure 5:
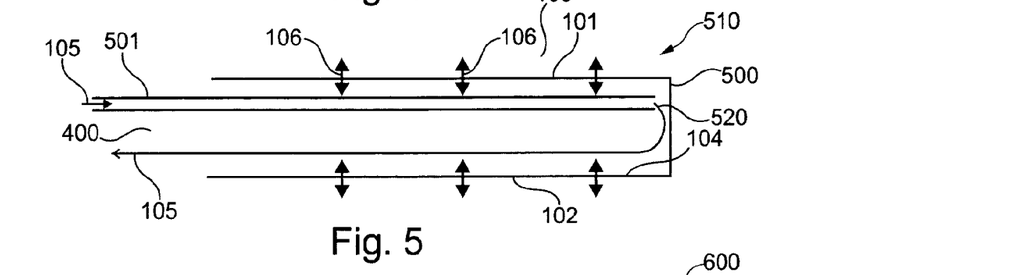

In contrast to this, FIG. 5 shows a so-called concentric configuration in which the outlet portion 401 of FIG. 4 is closed by a wall 500.

The perfusate 105 is inserted in an interior of the tube 101 via a separate tube 501. After equilibration with diffused components of the sampling fluid 103, the dialysis fluid 105 leaves the device 510 via the inlet channel 400 for further analysis. As can be taken from FIG. 5, the inner tube 501 extends almost to the wall 500 and may comprise an outlet 520 close to the end 500. Alternatively, the inner tube 501 may extend entirely to the wall 500 and may comprise a lateral outlet. In the shown embodiment, the inner tube 501 is used as an inlet, but may alternatively be used as an outlet as well.

Figure 6:
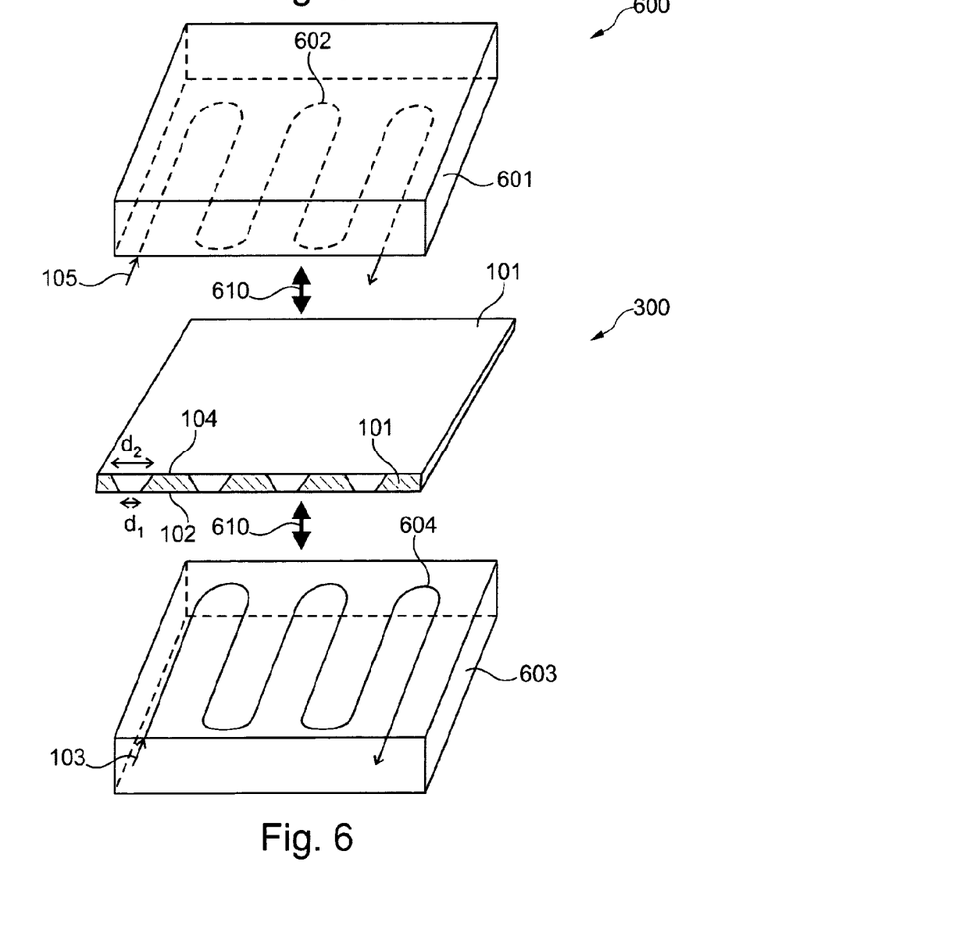

In the following, referring to FIG. 6, an apparatus 600 for analyzing a sampling fluid 103 according to an exemplary embodiment of the invention will be explained.

The apparatus 600 comprises the sheet-like device 300 shown and described referring to FIG. 3.

Furthermore, a fluid transport unit (not shown), namely a pump, is adapted to pump a perfusate 105 through the system. This (or a separate) fluid transport unit may further be adapted to pump the sampling fluid 103 through the apparatus 600.

The apparatus 600 comprises a first cuboid substrate 601 made of a plastic material and having a first meandrous fluidic path 602 milled in a lower surface of the plastic substrate 601. Furthermore, a second cuboid plastic substrate 603 is provided having a second meandrous fluidic path 604 milled in an upper surface portion of the second substrate 603. Other shapes as cuboids are possible for members 601, 603. When the first substrate 601 is mounted to the second substrate 603 with the device 300 being sandwiched in between (see arrows 610), the sampling fluid 103 is pumped through the meandrous substrate 604 and may be brought in interaction, via the membrane 300, with a perfusate flowing through the meandrous fluidic path 602. As can be taken from the direction of the arrows in FIG. 6, the fluids flow in the meandrous fluidic paths 602 and 604 in concurrent manner. However, a countercurrent flow is possible as well in alternative embodiments.

In the following, referring to FIG. 7, a system 700 will be explained in which a device according to an exemplary embodiment of the invention is embedded.

The system 700 allows to continuously monitor the glucose concentration of an intensive care patient.

A body interface 100 as described above referring to FIG. 1 is implanted into the body of a human intensive care patient 701 accessing the sampling fluid of interest. The device 100 provides for a dialysis fluid into which glucose diffuses from the sampling fluid according to the glucose concentration of the patient 701. This modified dialysis fluid 702 is supplied to a sensor system 703 for detecting the glucose level in the modified dialysis fluid 702, and allowing to derive information regarding the glucose level of the patient 701.

A processor unit 704 is supplied with the results of the sensing by the sensor 703, and is supplied with intensive care unit data provided by a unit 705. Furthermore, the processor 704 has access to a data pool 706 to get further information. The main platform 704 may also access an algorithm unit 707 providing calculation algorithms. Based on all this information, the control unit 704 calculates whether infusing glucose and/or insulin is necessary, and supplies this infusion data 708 to an infusion unit 709. The infusion unit 709 may then administer a corresponding amount of glucose or insulin to the patient 701.

Figure 7:
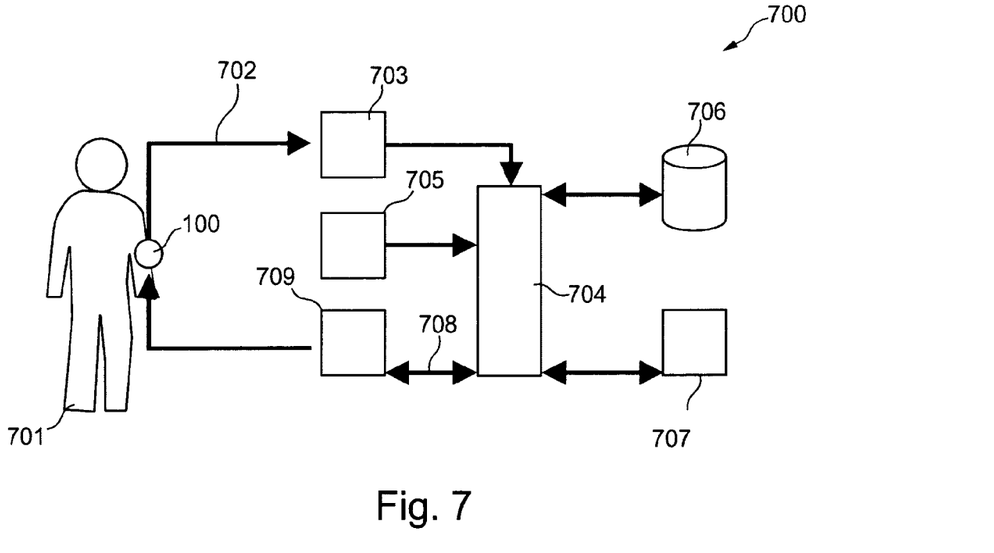
FIG. 7 shows an apparatus including a device according to an exemplary embodiment of the invention.

Although not shown in FIG. 7, a perfusate supply conduit may be provided as well. This may be required when the body interface 100 is adapted as a microdialysis device. The supply line in FIG. 7 serves as an infusion line for a medication (insulin/glucose).

In the following, microdialysis and ultrafiltration applications using probes with special characteristic features according to exemplary embodiments of the invention will be explained.

Longevity as well as long-term stability and performance of microdialysis/ultrafiltration probes strongly depend on the probe being used. Conventional microdialysis/ultrafiltration probes provide no functional customization for its intended use in special tissues or organs nor functionalization regarding antimicrobial, antibacterial, anti-inflammational, anti-coagulational or anti-adhesive features. In this application, the use of microdialysis/ultrafiltration probes with site, tissue or organ specific characteristic features are disclosed which make its application superior to conventional microdialysis/ultrafiltration probes in terms of longevity, long-term and mechanical stability, antimicrobial, antibacterial, anti-inflammational, anticoagulational and anti-adhesive features.

Microdialysis is a well established scientific tool. All mentioned arguments provided in this description referring to microdialysis can also be applied for ultrafiltration except otherwise noted. A first application of microdialysis has been described in the field of brain research in the 1970s. Other tissues like subcutaneous tissue, muscle and organs have been investigated in animal models and humans using microdialysis.

In recent years researchers have also switched to apply microdialysis in blood vessels to have direct contact to the true, free concentration of metabolites and drugs in the most representative organ. First, pharmacokinetic and pharmacodynamic studies have been performed in animals. In the meantime intravenous microdialysis is a well-established scientific tool and it is used mainly in animal models. The application of blood microdialysis in man may be limited because the risk associated with implanting a probe into a blood vessel is still higher compared with the risk involved in probe implantation into organs or interstitial space (subcutaneous, intramuscular or adipose tissue). However, with the recent development of flexible and robust probes that can be easily sterilized and that are introduced in arteries/veins of patients using standard clinical procedures, microdialysis in human's whole blood has become feasible and a few reports demonstrating the use of blood microdialysis have been published, first in the 1990s. Intravascular microdialysis has been used for monitoring of metabolites as well as monitoring of pharmacokinetics. The performance and the patient's comfort with the devices have been described as excellent compared to frequent blood withdrawal. However, it is believed that there are no studies describing microdialysis/ultrafiltration in humans for more than 24 hours.

It will become clear in the following discussion that there is a certain need for performing long term (particularly longer than 24 hours) intravascular microdialysis/ultrafiltration and that therefore it is necessary to have a vascular microdialysis/ultrafiltration device, which is improved or optimized regarding blood compatibility and thrombogenity in terms of material choice, surface and structural modification, any kind of heparin binding or synthetic imitation of the glycocalix, or other the like; in general, any method that reduces, limits or prevents fouling and/or the activation of the coagulation cascade in the investigated subject. Besides these effects the diffusion characteristics of metabolites and drugs from blood to the dialysis fluid inside the membrane may be improved or optimized with the afore mentioned modifications with respect to stability in long term investigations.

The herein given discussion is mostly dedicated to vascular microdialysis/ultrafiltration, but exemplary embodiments of the invention are not limited to vascular microdialysis/ultrafiltration alone, but include in general all tissues and organs. Any probe, which is applied in tissue or organ should have special characteristic features which makes it "biocompatible". When performing blood microdialysis/ultrafiltration, for example, the device may have anticoagulational characteristics. When performing microdialysis/ultrafiltration in other tissues or organs probes with special antimicrobial, antibacterial and anti-inflammational features may be advantageous. An anti-adhesive coating may also be advantageous with regard to membrane fouling and probe longevity or when monitoring sticky biological substances or drugs.

Now, general advantages of microdialysis/ultrafiltration will be explained. Special advantages of vascular microdialysis will be given subsequently.

An important advantage of microdialysis in general is that it gives continuous information about the unbound concentration of the analyte of interest and online sensing is therefore possible. The extracted samples are protein free, so there is no need for post sampling preparation. No centrifugation, no enzymatic action, protein degradation, etc.

Generally, sampling can be performed continuously without fluid loss, obtaining high resolution concentration profiles of drugs and metabolites (see Flexible intravenous microdialysis probe for blood sampling in freely moving rats, Pedro Rada, Marco Parada and Luis Hernandez, Journal of Applied Physiology, 1993, Vol. 74:466-469). This makes it a powerful tool for the determination of pharmacokinetic parameters of drugs without interfering with the process that governs the pharmacokinetic behaviour of the drug (see Blood microdialysis in pharmacokinetic and drug metabolism studies, Roger K. Verbeeck, Advanced Drug Delivery Reviews, 2000, Vol. 45:217-228), giving the possibility to reduce the number of subjects needed, compared with methods that involve post mortem analysis at several single time points after drug administration, in which each animal provides only a single time point (see Methodological issues in microdialysis sampling for pharmacokinetic studies, Elisabeth C M de Lange, A G de Boer and Douwe D, Breimer Advanced Drug Delivery Reviews, 2000, Vol. 45:125-148).

A general overview of characteristics and resulting advantages of microdialysis and ultrafiltration is given as well by Table 1 of Garrison et al. (A review of membrane sampling from biological tissues with applications in pharmacokinetics, metabolism and pharmacodynamics, Kenneth E Garrison, Stephanie A Pasas, Joshua D Cooper and Malonne I Davies, European Journal of Pharmaceutical Sciences, 2002, Vol. 17:1-12).

Considering vascular microdialysis/ultrafiltration in concrete, a list of important features is given by Patsalos et al. (Antiepileptic Drug Pharmacokinetics in Patents with Epilepsy Using a New Microdialysis Probe: Preliminary Observations, P N Patsalos, M T O'Connell, H C Doheny, JWAS Sander and S D Shorvon, Acta Neurochirurgica, Supplement, 1996, Vol. 67:59-62):

No blood sampling occurs and thus no net fluid (blood) loss (Repetitive blood sampling represents a change in the blood volume which in turn results in a change of the hemodynamic status of the experimental animal/proband/patient)

No need for constant flushing of catheter to maintain patency and thus no fluid gain No use of systemic heparinization is necessary, which can affect drug pharmacokinetics, to maintain catheter patency (comment: Heparin used to maintain catheter patency has been shown to change blood chemical content, see Flexible intravenous microdialysis probe for blood sampling in freely moving rats, Pedro Rada, Marco Parada and Luis Hernandez, Journal of Applied Physiology, 1993, Vol. 74:466-469)

Monitoring of the "free" pharmacologically active fraction is achieved (comment: not the total concentration of a drug will be recovered but only the pharmacologically active "free" concentration of a drug. The "non-free" amount of drugs is bound to proteins for example and is therefore not active.)

Enzymes and proteins are excluded from microdialysate and thus post-sampling degradation of the analytes is diminished (comment: Measurements of hormones in the blood require the inactivation of degradative enzymes. To accomplish this inactivation, blood must be initially centrifuged and then deproteinized, see Flexible intravenous microdialysis probe for blood sampling in freely moving rats Pedro Rada, Marco Parada and Luis Hernandez Journal of Applied Physiology; 1993; Vol. 74:466-469)

Sample preparation prior to analysis can be greatly simplified

Next, general disadvantages of microdialysis/ultrafiltration will be explained:

Implantation of the probe may elicit tissue reactions which may interfere with the system under investigation.

There is a risk of infection associated with the implantation of a microdialysis/ultrafiltration probe Lipophilic drugs may stick to tubings and probe components The dialysis procedure will in general not yield equilibrium in the dialysate compared to the surrounding medium (recovery <100%). Performing ultrafiltration will yield in 100% recovery anyway.

It can be assumed that the in vivo recovery of an analyte is not stable over time, especially when performing long term experiments. So it is of great importance to monitor the recovery. There are several methods for monitoring the recovery of a membrane: retrodialysis, internal standard and ionic reference (see U.S. Pat. No. 7,022,071 B2). This may have the advantage that the recovery can be determined online via a simple conductivity measurement.

To overcome the problem of instable or decreasing recovery rates probe characteristics according to exemplary embodiments of the invention may for example feature to have the selective layer (smooth surface) on the outside to use membrane(s) having an asymmetrical wall structure, e.g. a membrane, having a small pore size (=high mass density) on the surface in contact with the fluidic sample while having a higher pore size (=lower mass density) on the surface in contact with the dialysis fluid to use membrane(s) having a rough surface in contact with the dialysis fluid to prevent laminar flow/enhance turbulent flow in order to increase the diffusion behaviour across the membrane(s)

to use surface treatments/coatings for probe materials with coating or surface mimicking techniques in order to obtain antibacterial, antimicrobial anti-inflammational and/or anti-adhesive behaviour to reduce the risks and problems generally associated with implantation, like inflammation, bacterial growth, rejection reactions and fouling as well as the associated problems and risks like reduced analyte recovery, ephemerality of the probe, clotting of vessels and thrombosis As a result these modifications in material choice and surface modification will contribute to an outstanding bio- and hemocompatibilty while at the same time enabling stable, long term monitoring of analytes.

In addition to the above mentioned risks associated with microdialysis/ultrafiltration, there is one major risk associated with vascular microdialysis/ultrafiltration, in concrete. If the membrane breaks inside the vessel and parts of the membrane get lost in the blood stream, there is a high risk of thrombosis or even embolism, maybe resulting even in an infarct. Therefore it is also a purpose of embodiments of the invention to use membranes with improved mechanical stability for such devices. However, the new developed flexible membranes and tubings that are used when vascular microdialysis/ultrafiltration is performed may reduce or minimize the risk of membrane damage and/or disruption.

In the following, conventional microdialysis/ultrafiltration probes/catheters will be explained.

The following list gives an overview of current embodiments of microdialysis and ultrafiltration probes. These embodiments describe probes, applications and methods to which embodiments of this invention relate and can be applied: U.S. Pat. No. 4,777,953, WO 99/45982, U.S. Pat. Nos. 6,030,358, 5,002,054, 5,191,900, 4,694,832, 5,706,806, 4,516,580, 4,274,417, 4,221,567, 6,478,767, 5,607,390, 5,372,582, 6,346,090, and U.S. Pat. No. 6,805,683 B1, U.S. Pat. No. 5,106,365, WO 2004/033000, U.S. Pat. No. 6,591, 126, WO 01/03752, WO 03/055540, WO 2004/032735, U.S. Pat. No. 4,274,417, WO96/14889, WO95/20991. All embodiments disclosed in these patents may serve as a basis for designing sample monitoring device according to exemplary embodiments of the invention.

In the following, some conventional probes will be defined explicitly. These probes may be used in combination with (membrane) devices according to exemplary embodiments of the invention. Consequently, the following embodiments are explicitly included in the disclosure of this patent application:

FIG. 1 of Blood microdialysis in pharmacokinetic and drug metabolism studies, Roger K. Verbeeck, Advanced Drug Delivery Reviews; 2000; Vol. 45:217-228. This figure shows an example for a linear (above) and a concentric (below) probe design.

FIG. 9A, 9B of U.S. Pat. No. 6,478,767 Bland FIG. 2 of U.S. Pat. No. 6,346,090 B1. These embodiments relate to a probe design using two or more hollow fibres, one or more for the delivery of perfusate to the probe and (the others) for transporting dialysate out of the probe.

FIG. 11 of U.S. Pat. No. 6,478,767 B1, FIG. 1 of WO9218191 and FIG. 1B of U.S. Pat. No. 5,002,054. These embodiments relate to a loop type embodiment of a microdialysis probe. The hollow fibre membrane(s) are bent in a U-shape, so that one end of the fibre can be used as entrance for the perfusate whereas the other end of the same fibre is used as exit for the perfusate. So entrance and exit are in the same site. This is in contrast to another form of linear microdialysis devices which also use the two ends of one fibre as entrance and exit of perfusate and dialysate, respectively, but the membrane is not bent so the ends are in opposite direction and the microdialysis/ultrafiltration device has to be threaded through the tissue where microdialysis/ultrafiltration should be performed, compare (FIG. 1 of U.S. Pat. No. 5,706,806A1: linear MD probe).

The first probes that were routinely used for implantation in the central nervous system were of the concentric type and were constructed of stainless steel needle tubing, fused silica and a semi-permeable membrane. However, performing experiments in freely moving animals after implantation of such a rigid probe into a blood vessel or other peripheral tissues may be not ideal since the probe, especially the semi-permeable membrane, may be damaged or alternatively the steel parts may cause excessive damage to the tissue/organ. Therefore, flexible microdialysis probes were constructed in the early 1990s to allow the application of microdialysis sampling to sites other than the brain (see Blood microdialysis in pharmacokinetic and drug metabolism studies, Roger K. Verbeeck, Advanced Drug Delivery Reviews, 2000, Vol. 45:217-228).

Next, aspects related to vascular microdialysis/ultrafiltration will be explained.

One exemplary aspect of a new type of vascular microdialysis/ultrafiltration is to have a standard blood vessel catheter into which a microdialysis/ultrafiltration-probe (including tubings for perfusate transport and membrane) is plugged, for instance with a Luer lock.

In the scientific literature the majority of probes are inserted into a blood vessel catheter in a way that the membrane protrudes the catheter's tip and is in direct contact with blood. This technique allows for easy and mechanically less stressful setting and replacement of the probe.

But there are several other embodiments of performing vascular microdialysis/ultrafiltration (see WO 99/45982, U.S. Pat. Nos. 4,516,580, and 5,607,390, U.S. Pat. No. 6,346, 090 B1).

In the following, examples of how vascular microdialysis/ultrafiltration devices can look like and how they are implanted into the vascular system will be defined explicitly. These systems may be used in combination with (membrane) devices according to exemplary embodiments of the invention. Consequently, the following embodiments are explicitly included in the disclosure of this patent application:

FIG. 1 of Human Pharmacokinetics of L-3,4-Dihydroxyphenylalanine Studied with Microdialysis, Nil Dizdar, Anita Kullman, Björn Norlander, Jan-Edvin Olsson and Bertil Kagedal, Clinical Chemistry, 1999, Vol. 45(10):1813-1820.

FIG. 1 of Blood microdialysis in humans: A new method for monitoring plasma compounds, Ximena Paez and Luis Hernandez, Life Sciences, 1997, Vol. 61:847-856.

In the recent past a few new groups have applied vascular microdialysis/ultrafiltration for monitoring pharmacokinetics.

For flowing fluid systems like blood, an in vitro calibration can provide valuable in vivo recovery values if perfusion flow-rate and temperature are well controlled, provided that the characteristics of the membrane do not change upon implantation and/or during the experiment. However, here also physiological responses to probe implantation, which may result in changes to the membrane environment, for example, clot formation around intravenously implanted probe may occur (see Methodological issues in microdialysis sampling for pharmacokinetic studies, Elisabeth C M de Lange, A G de Boer and Douwe D Breimer, Advanced Drug Delivery Reviews, 2000, Vol. 45:125-148). This may yield in a formation of a diffusive hindering layer around the membrane possibly resulting in a decrease of relative recovery. Occlusion of membrane pores by cells or sticky drugs (medication of patient; ICU, etc.) or metabolites may also occur resulting again in a decrease of relative recovery. Other physiologic reactions to probe implantation are of course inflammation, bacterial growth and probe rejection reaction.

For intravenous implantation of the probe, blood clotting around the dialysis fibre is very likely to occur. 24 h after implantation into the vena cava of the rat, a fibrin sheath was present around a regenerated dialysis fibre, however, the presence of this fibrin sheath did not affect recovery of the analyte (flurbiprofen) by the probe up to 48 h following implantation. After 48 h of implantation, however, the in vivo recovery characteristics of the probe gradually decreased (see Blood microdialysis in pharmacokinetic and drug metabolism studies, Roger K. Verbeeck, Advanced Drug Delivery Reviews, 2000, Vol. 45:217-228).

Also Chen et al (see Plasma Microdialysis: A technique for continuous plasma sampling in freely moving rats, Chen Z and Steger R W, Journal of Pharmacological and Toxicological Methods, 1993, Vol. 29(2):111-118) reported that membrane permeability to glucose of a microdialysis probe (regenerated cellulose dialysis fibre) implanted in the right atrium of the rat rapidly decreased (comment: the recovery decreased within 5 hours after implantation which is certainly less than 48 hours reported by Verbeeck et al., see Blood microdialysis in pharmacokinetic and drug metabolism studies, Roger K. Verbeeck, Advanced Drug Delivery Reviews, 2000, Vol. 45:217-228) following implantation unless the rats were heparinised.

Yang et al (see The design and validation of a novel intravenous microdialysis probe: Application to fluconazole pharmacokinetics in the freely-moving rat model, Yang H, Wang Q and Elmquist W F, Pharmaceutical Research, 1997, Vol. 14(10):1455-1460) also found a steady decline in the in vivo recovery over a 10-day period of their home-made microdialysis probes starting after the implantation into the inferior vena cava of the rat.

These findings are in line with the results of others (see Antipyrine as a dialyzable reference to correct differences in efficiency among and within sampling devices during in vivo microdialysis, Yokel R A, Allen D D, Burgio D E and McNamara P J, Journal of Pharmacological and Toxicological Methods, 1992, Vol. 27(3):135-142; Application of microdialysis to the pharmacokinetics of analgesics: Problems with reduction of dialysis efficiency in vivo, Sauernheimer C, Williams K M, Brune K and Geisslinger G, Journal of Pharmacological and Toxicological Methods, 1994, Vol. 32(3):149-154)). Sauernheimer et al. compared the recovery of microdialysis probes placed in the vein of rats to microdialysis probes placed into NaCl and anticoagulated blood in an in vitro setup. Despite their finding that the recovery of the in vivo placed microdialysis probe started to decrease 5 hours after implantation ending up with a recovery of about 50% after 17 hours of operation they also found a decline in recovery with heparinized blood in vitro from 93.7% to 49.2% within 20 hours. In addition they found no decrease in recovery when investigating the long term stability of the probe in NaCl. The recovery remained stable at 88.3-93.0% for 40 hours.

This reduction in recovery may be attributed to fibre clotting and changes in probe properties due to plasma protein and/or cell deposition on the surface of the membrane. A similar phenomenon has been observed in clinical hemodialysis studies and was found to be dependent on the type of dialysis membrane being used and the type of analyte studied (see Effect of blood-membrane interactions on solute clearance during hemodialysis, Langsdorf L J, Krankel L G and Zydney A L, ASAIO Journal, 1993, 39(3):M767-772).

All of these results (especially the in vitro results of Sauernheimer et al, Application of microdialysis to the pharmacokinetics of analgesics: Problems with reduction of dialysis efficiency in vivo, Sauernheimer C, Williams K M, Brune K and Geisslinger G, Journal of Pharmacological and Toxicological Methods, 1994, Vol. 32(3):149-154)) are in contrast to the findings of the inventors of the present invention which have been achieved using microdialysis/ultrafiltration probes with new characteristic features which make the probe specially suitable to perform microdialysis/ultrafiltration in blood. The recovery remained stable for 120 hours of continuous operation in anticoagulated blood in vitro. This difference in recovery behaviour can be directly attributed to the use of a probe with special characteristic features, according to the latter mentioned parameters.

Figure 8:
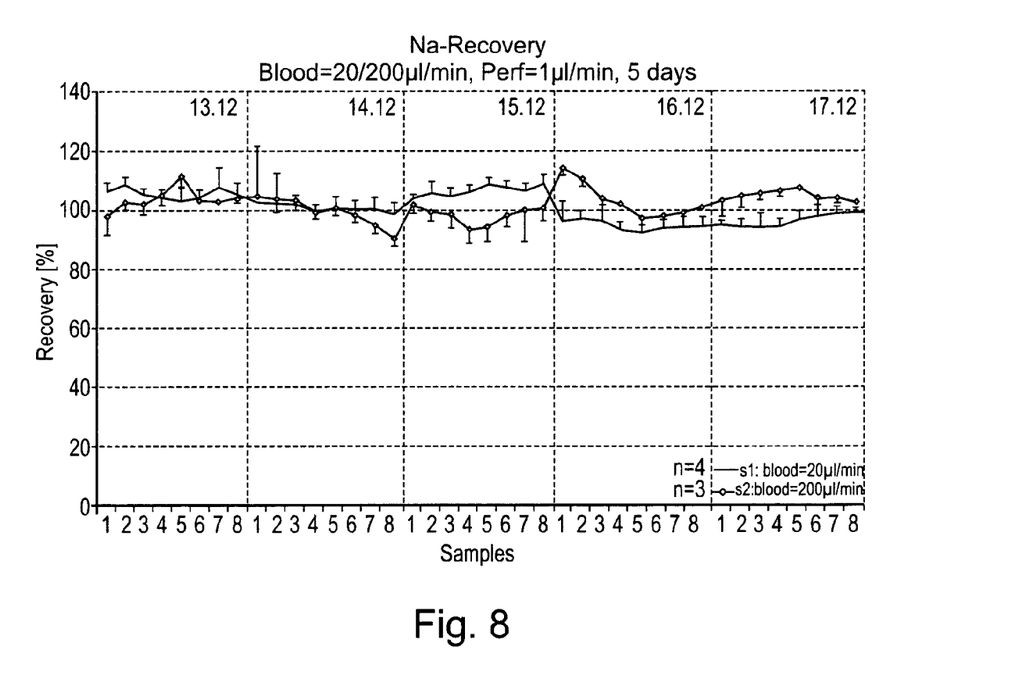
FIG. 8 shows a diagram illustrating time stability of a device according to an exemplary embodiment of the invention.

FIG. 8 illustrates results from in vitro investigations of the inventors using structurally improved microdialysis/ultrafiltration probes in bovine blood. As can be taken from the diagram of FIG. 8, recovery remains stable for 120 hours.

Summing this all up, it is possible to say that important progress has been made during this short period of time that microdialysis/ultrafiltration is being used intravascularly, in areas such as probe design, calibration of the probes, simultaneous use of multiple probes and evaluation of the sampling technique during long-term implantation. Especially this last issue is important as long-term experiments with implanted probes do not yield in stable recovery profiles.

As a consequence of the general necessity and importance of vascular microdialysis/ultrafiltration and its lack in performing stable over more than several hours (e.g. more than 24 hours), the herein described invention discloses embodiments of a tool that is capable of performing stable long term intravascular microdialysis/ultrafiltration. This tool may make use of all applicable embodiments of microdialysis/ultrafiltration probes and may reconfigure them by adding new characteristic features, that will be described in more detail in the following. On the basis of the disclosure of this patent application, the skilled person is enabled to modify a plurality of conventional embodiments accordingly, to obtain the described results.

Results obtained by the inventors have shown that using such specially designed probes for microdialysis/ultrafiltration applications in blood yields promising results in vitro regarding long-term stability of membrane recovery. So as a consequence, better performance of in vivo probes can be expected compared to conventional approaches regarding long term stability of membrane recovery.

Beyond the improvement in recovery-stability of microdialysis/ultrafiltration probes also tissue responses (like encapsulation, coagulation, fouling) may be reduced or prevented using probes of the herein given embodiments. Furthermore the improvement of the mechanical stability of the fragile membrane makes its use superior for intravascular microdialysis/ultrafiltration compared to conventional microdialysis/ultrafiltration membranes.

So using such a specially designed probe when performing vascular microdialysis/ultrafiltration may reduce the risk of coagulation and will therefore not only improve the quality of the measurement but may also reduce the health risk for the patient associated with such a vascular microdialysis/ultrafiltration device.

Next, material, properties and surface modifications of membranes according to exemplary embodiments of the invention will be explained.

The choice of the membrane type is an essential element in designing an improved or optimal probe for a particular application. It is further more of importance that the membrane (but also other material like tubing connections etc) do not interact with the analyte and the surrounding medium (see Methodological issues in microdialysis sampling for pharmacokinetic studies, Elisabeth C M de Lange, A G de Boer and Douwe D Breimer, Advanced Drug Delivery Reviews, 2000, Vol. 45:125-148).

According to exemplary embodiments of the invention, membranes can be planar or hollow fibre membranes. Appropriate materials include: Cellulose, Copolymer (polyacetronitrile/sodium methallyl sulfonate), Copolymer (polycarbonate/polyether), Acrylic copolymer, Polysulfone, Cuprophane, Polyarylethersulphone (PAES), Polyethersylfone (PES), Polycarbonate (PC), PAN. Still other possible membrane materials may include inorganic materials like Ceramic, Glass, Stainless steel or derivatized carbon.

Microdialysis/ultrafiltration probes can be bought commercially from different providers (CMA, Bioanalytical, Microbiotech, etc.) or they can be homemade, which is the most convenient and the cheapest way of doing microdialysis/ultrafiltration.

No matter how to get the probe, for biocompatibility reasons it is possible to use membranes whose origin or intended application is dialysis. So these membranes are now intended to perform microdialysis/ultrafiltration where different requirements would have to be met.

Whereas blood dialysis intends to perform high analyte flux from one side of the membrane to the other side to wash out certain drugs or metabolites with microdialysis/ultrafiltration it is of importance to get a (partial) equilibrium between the two separated phases and the driving force behind this analyte exchange is diffusion and osmosis.

In dialysis machines blood is flowing inside the hollow fibre membranes and the perfusate is running outside the fibres. When performing vascular microdialysis/ultrafiltration (intra- or extracorporeally) it is the other way round. Blood will be outside the membrane whereas the perfusate will be on the inside of the membrane.

The surface of membranes that are used in dialysing machines provides a smooth surface with small pore size on the inner lumen and a rougher surface on the outside. This may be important in terms of cell adhesion to the inner lumen pores, resulting in a recovery decrease. So for a membrane being used in vascular microdialysis/ultrafiltration it would be consequent to have the membrane inverted, to have the smooth surface (which will be in contact to blood) on the outside. This will reduce the probability of cell adhesion to the surface which in turn would result in a reduced likelihood of recovery decrease.

Besides that, dialysis patients may be heparinized during the dialysis process so that extracorporeal blood coagulation in the dialysing machine may be suppressed. Such coagulation—happening inside membranes—will of course influence the recovery characteristics of the membrane if it does not block the membranes anyway. When performing vascular microdialysis/ultrafiltration heparinization of the patient/proband may be not advisable considering the risks associated with anticoagulation. Therefore it is possible to have a heparin coating on the outer surface of a microdialysis/ultrafiltration membrane but also a coating of all surfaces which are in direct contact with blood (tubing, catheter, adhesive surfaces, etc.). This may reduce the probability of coagulation and/or fibrin and/or clot formation on and/or around the microdialysis/ultrafiltration probe.

Out of these considerations it may be advantageous to improve the membranes and other materials which are in contact with blood for use in vascular microdialysis/ultrafiltration.

Currently available membranes are actually made and intended for use in dialysis machines where blood flows inside the hollow fibre. Therefore the surface structure of such membranes has to be modified regarding cell adhesion and dialysis efficiency on the inner surface, in such a way that pore size and structure of the inner wall of the hollow fibre contribute to a smooth surface, preventing or at least reducing cell adhesion, for example. This side of the membrane having the smooth surface may be called the selective layer, because it enables the passage of small molecular weight substances while it hinders the diffusion of larger molecular weight substances. This particular pore size is called molecular weight cut off (MWCO). It typically lies in the range between 5.000 and 100.000 Dalton.

Applying membranes in vascular microdialysis/ultrafiltration should therefore consequently mean to use different membranes, i.e. membranes having the selective layer (=smooth skin) on the outside as blood is surrounding the membrane.

Next, aspects related to a functionalization of the membrane will be explained:

One feature of the membrane is not to activate cellular and non-cellular blood components by means of e.g. coagulation.

So heparinization is an additional excellent means to improve biocompatibility, i.e. thromogenecity of the membranes used for vascular microdialysis/ultrafiltration with direct blood contact.

But there are also other methods to "functionalize" a membrane considering bio- and hemocompatibility. Thus, embodiments of the invention are not limited to the use of a single specially functionalized membrane but the scope of protection governs the use of membranes with all possible techniques to "functionalize" its surface.

These methods include coating technologies with immobilised agents as well as drug eluting agents and mimicking technologies. A couple of them will be mentioned below (see Effect of blood-membrane interactions on solute clearance during hemodialysis, Langsdorf L J, Krankel L G and Zydney A L, ASAIO Journal, 1993, 39(3):M767-772).

Coatings may use a number of methods to ensure blood compatibility. Some coatings rely on biologically active materials loaded into a polymer matrix or bonded to the device surface. These bioactive materials prevent clot formation by altering the physiological responses of blood.

Another possibility may boost the anticlotting effects of heparin molecules, which are chains of repeating sugar units. Each chain includes an active sequence of five sugar residues that bind to and accelerate the activity of antithrombin, a clot-preventing agent in the blood. If a coating process attaches this active sequence to a device surface, it will hamper the heparin molecule's ability to interact with the blood (CBAS coating by Carmeda).

Therefore, CBAS features end-point attachment of heparin molecules. Fastened at their end points to a device surface, the molecule's way in the bloodstream is like seaweed in water, according to Carmeda. This improves or maximizes the interaction between the active sequence and the flowing blood.

For greater durability, CBAS covalently bonds heparin to a device surface. Unlike heparin-release coatings, which are effective only as long as the drug supply lasts, the bonded heparin is not depleted over time. Thus, a fixed amount of the drug can continue to fight clotting for as long as several months.

There are other ways to boost hemocompatibility besides employing clot-fighting agents like heparin. One is to disguise the device surface so blood can not detect the presence of foreign material and trigger clot formation.

AST Products inc. is working on a bioinert coating designed to provide blood compatibility without bioactive agents like heparin. Instead, the coating will include a substance that attracts and binds blood proteins to a device surface. The proteins will cover the coated surface, hiding it from the blood-stream and thereby preventing clot formation.

Another surface-disguising coating which has already reached the market has been developed by Hemoteq GmbH (Würselen, Germany), the appropriately named Camouflage coating provides hemocompatibility by mimicking endothelial cells that line human blood vessels. Camouflage consists of a single layer of molecules with a thickness measured in nanometers. To ensure durability, the coating is attached to a device by a covalent bonding process.

Like Camouflage, a coating from MC3 Inc. (Ann Arbor, Mich.) mimics human endothelial cells. But the MC3 coating takes a more active approach to mimicry. According to MC3, tests have shown that endothelial cells generate nitric oxide (NO), which prevents the platelet activation that causes clotting in blood vessels. To mimic this natural anticlotting action, it is possible to use NO-releasing polymers that can be used to coat medical devices.

Because NO and heparin work on different parts of the clotting process, it is believed that the most effective blood-compatibility approach would be to combine both anticlotting agents in a single coating.

It is also possible to implement new factors that might enhance hemocompatibility. For example, antimicrobial additives may kill bacteria that cause thrombus formation.

It is also possible to use genes that give hemocompatibility-enhancing instructions to the body. For instance, genes in a coating can signal the endothelium to get cranking real fast or trigger the production of cells that mask an implanted device from the blood.

It is also possible to have artifical coatings with cells. The herein mentioned coating methods are disclosed, as such, on http://www.wleventon.com/fcoat.html, for instance.

These mentioned probe "functionalisations" govern the application of microdialysis/ultrafiltration especially in blood. But there are also other site, tissues or organs where microdialysis/ultrafiltration can be performed, and actually microdialysis/ultrafiltration probes may be adopted according to their site of application. This includes antimicrobial and antibacterial and anti-inflammational and anti-adhesive material treatments.

Embodiments of the present invention relate to microdialysis and ultrafiltraion and combine the technique of current microdialysis/ultrafiltration embodiments with the use of materials that are specially designed for their application in organs and tissues including blood and the interstitial fluid as well as bones and any other accessible body compartment, by means of material's surface and/or morphology modification/adoption (rigidness of materials, and/or membrane "functionalization" in any of the manners described in the definition of "functionalization" above). Using microdialysis/ultrafiltration devices with these special characteristics, for example in the vascular system, may improve long term stability of the analyte recovery and thereby quality of the obtained results and longevity of the probe, as has been shown in studies of the inventors in contrast to current vascular microdialysis/ultrafiltration applications that do not make use of such special characteristic probe features for their studies and therefore yield in bad recovery stability and bad longevity of the probes, as already mentioned in chapter above.

Using probes according to exemplary embodiments of the invention with at least one of the herein mentioned surface and/or morphology modifications ("functionalizations") may improve the probe's longevity, the probe's recovery and mechanical stability and will at the same time also reduce the risks and problems generally associated with implantation, like inflammation, bacterial growth, fouling and rejection reactions.

Probe "functionalizations" according to exemplary embodiments of the invention may for example feature
- to have the selective layer (smooth surface) on the outside
- to use membrane(s) having an asymmetrical wall structure, e.g. a membrane, having a small pore size (=high mass density) on the surface in contact with the fluidic sample while having a higher pore size (=lower mass density) on the surface in contact with the dialysis fluid
- to use a membrane(s) having a rough surface in contact with the dialysis fluid to prevent laminar flow/enhance turbulent flow in order to increase the diffusion behaviour across the membrane(s)
- to use surface treatments/coatings for probe materials with coating or surface mimicking techniques in order to obtain antibacterial, antimicrobial anti-inflammational and/or anti-adhesive behaviour to reduce the risks and problems generally associated with implantation, like inflammation, bacterial growth, rejection reactions and fouling as well as the associated problems and risks like reduced analyte recovery, ephemerality of the probe, clotting of vessels and thrombosis
- to have materials with adequate mechanical features (rigidity and flexibility) of the used materials according to the site of measurement (compare microdialysis in blood, microdialysis in muscle, microdialysis in bones)
- to adapt surface charge properties of the membrane, i.e. to make the membrane electrically charged or neutral As a result these "functionalizations" will contribute to an outstanding bio- and hemocompatibilty while at the same time enabling stable, long term monitoring of analytes and provide a high mechanical stability to the probe.

In the following, an exemplary field of application of devices according to embodiments of the invention will be explained.

In a study by Greet van den Berghe (Intensive insulin therapy in the critically ill patients, van den Berghe G, Wouters P, Weekers F, Verwaest C, Bruyninckx F, Schetz M, Vlasselaers D, Ferdinande P, Lauwers P, Bouillon R. N, Engl J Med, 2001, 345(19):1359-67) it could be shown that tight glycemic control of intensive care patients coming from major surgeries results in a significant reduction of morbidity and mortality by about 40%. Embodiments of the invention contribute to implement this tight glycemic control in the ICU. It is therefore necessary to continuously measure the glucose level in the patients to adequately calculate and infuse the desired amount of insulin/glucose needed. A measuring device, based on microdialysis and subsequent glucose sensing may be implemented. One of the target organs, where microdialysis information should be gathered from is the adipose tissue. As it is not known until now, whether this tissue represents the true glucose concentration, it is tried to perform microdialysis intravascularly, so to say directly in the blood stream of the patient.

The measurement shall give continuous glucose information for at least 72 hours. Therefore it is necessary that the involved components work reliably for this period of time. Current vascular microdialysis probes do not work proper for such long periods of time.

So it is one of the aims of embodiments of the invention to provide a vascular microdialysis/ultrafiltration device that is capable of operating reliably in the vascular system of an intensive care patient for at least 72 hours.

In the following, some other exemplary fields of application of embodiments of the invention will be given:
- pharmaceutical research: pharmacokinetics, pharmacodynamics, blood brain barrier, comparing drug concentration in blood vs. liver and bile may yield important information concerning the processes governing the transport of drugs and/or their metabolites from the hepatocytes to the circulation or to the bile canaliculi
- drug/metabolite monitoring: Critically ill patients, during operations, stationary patients, competitive sport (lactate monitoring), children (limited amount of blood volume that can be withdrawn for analysis)

vascular microdialysis/ultrafiltration in animal experiments with rats, mice or other animals or with limited total blood volume, to reduce the amount of sampled blood volume (safes animal lifes, less costs, better results)

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:

1. A microdialysis device for analyzing a fluidic sample, the microdialysis device comprising:
   a permeable membrane;
   wherein the permeable membrane has a first surface to be brought in contact with the fluidic sample to traverse the permeable membrane;
   wherein the permeable membrane has a second surface to be brought in contact with a dialysis fluid;
   wherein the first surface is smoother than the second surface so that a surface roughness of the first surface is smaller than a surface roughness of the second surface;
   wherein the permeable membrane comprises pores having a mean size which increases from the first surface towards the second surface;
   wherein the permeable membrane comprises a hollow tube an outer surface of the hollow tube forming the first surface;
   wherein the pores have a size at the first surface smaller than essentially 0.1 μm;
   wherein the pores have a size at the second surface in the range between essentially 0.1 μm and essentially 0.4 μm; and
   wherein the permeable membrane has a molecular cut-off in a range between 1 kDa and 100 kDa.

2. The device of claim 1,
   wherein the pores have a size at the first surface particularly in the range between essentially 0.05 μm and essentially 0.09 μm.

3. The device of claim 1,
   wherein the permeable membrane has a molecular cut-off particularly in a range between 5 kDa and 50 kDa, more particularly of substantially 10 kDa.

4. The device of claim 1,
   wherein the first surface is functionalized to maintain permeability of the permeable membrane for the fluidic sample when analyzing the fluidic sample.

5. The device of claim 4,
   wherein the first surface is functionalized in a manner to suppress deposition and activation of components of the fluidic sample on the first surface.

6. The device of claim 1,
   wherein the first surface is adapted to be brought in contact with blood, so that a part of the blood is enabled to traverse the permeable membrane.

7. The device of claim 1,
   wherein the second surface is free of a functionalization.

8. The device of claim 1,
   wherein the second surface is functionalized to maintain permeability of the permeable membrane for the fluidic sample when analyzing the fluidic sample and to prevent cell adhesion of sticky analytes to the second surface.

9. The device of claim 1,
   adapted for vascular microdialysis.

10. The device of claim 1,
    wherein the permeable membrane comprises pores having a mean size which increases continuously from the first surface towards the second surface.

11. The device of claim 1,
    wherein the permeable membrane comprises pores having a mean size which increases in a stepwise manner from the first surface towards the second surface, particularly by manufacturing the permeable membrane using a plurality of layers, each layer having a specific mean pore size.

12. A method of monitoring a parameter of a fluidic sample by microdialysis, the method comprising:
    bringing a first surface of a permeable membrane in contact with a fluidic sample to traverse the permeable membrane;
    bringing a second surface of the permeable membrane in contact with a dialysis fluid;
    wherein the first surface is smoother than the second surface so that a surface roughness of the first surface is smaller than a surface roughness of the second surface, the permeable membrane comprising a hollow tube, an outer surface of the hollow tube forming the first surface;
    wherein the permeable membrane comprises pores having a mean size which increases from the first surface towards the second surface;
    wherein the pores have a size at the first surface smaller than essentially 0.1 μm;
    wherein the pores have a size at the second surface in the range between essentially 0.1 μm and essentially 0.4 μm; and
    wherein the permeable membrane has a molecular cut-off in a range between 1 kDa and 100 kDa.

13. The method of claim 12, further comprising:
    monitoring an analyte concentration, particularly for glucose monitoring.

* * * * *